(12) United States Patent
Morein et al.

(10) Patent No.: US 9,901,634 B2
(45) Date of Patent: Feb. 27, 2018

(54) COMPOSITIONS COMPRISING ISCOM PARTICLES AND LIVE MICRO-ORGANISMS

(71) Applicant: NOVAVAX AB, Uppsala (SE)

(72) Inventors: Bror Morein, Uppsala (SE); Karin Lovgren Bengtsson, Uppsala (SE)

(73) Assignee: NOVAVAX AB, Uppsala (SE)

(*) Notice: Subject to any disclaimer, the term of this patent is extended or adjusted under 35 U.S.C. 154(b) by 0 days.

(21) Appl. No.: 14/933,722

(22) Filed: Nov. 5, 2015

(65) Prior Publication Data

US 2016/0114034 A1  Apr. 28, 2016

Related U.S. Application Data

(60) Continuation of application No. 14/146,365, filed on Jan. 2, 2014, now Pat. No. 9,205,147, which is a continuation of application No. 12/905,418, filed on Oct. 15, 2010, now abandoned, which is a division of application No. 10/550,026, filed as application No. PCT/SE2004/000451 on Mar. 24, 2004, now Pat. No. 7,838,019.

(30) Foreign Application Priority Data

Mar. 24, 2003 (SE) ...................... 0300795

(51) Int. Cl.
*A61K 39/39* (2006.01)
*A61K 39/155* (2006.01)
*C12N 7/00* (2006.01)
*A61K 39/145* (2006.01)
*A61K 39/00* (2006.01)

(52) U.S. Cl.
CPC ............ *A61K 39/39* (2013.01); *A61K 39/145* (2013.01); *A61K 39/155* (2013.01); *C12N 7/00* (2013.01); *A61K 2039/525* (2013.01); *A61K 2039/5252* (2013.01); *A61K 2039/55511* (2013.01); *A61K 2039/55577* (2013.01); *A61K 2039/70* (2013.01); *C12N 2760/16134* (2013.01); *C12N 2760/18634* (2013.01)

(58) Field of Classification Search
None
See application file for complete search history.

(56) References Cited

U.S. PATENT DOCUMENTS

| | | |
|---|---|---|
| 4,900,549 A | 2/1990 | De Vries |
| 5,676,354 A | 10/1997 | Okutsu et al. |
| 5,679,354 A | 10/1997 | Morein et al. |
| 5,753,235 A | 5/1998 | Haanes et al. |
| 5,925,359 A | 7/1999 | Van Woensel et al. |
| 6,177,081 B1 | 1/2001 | Wechter et al. |
| 7,838,019 B2 | 11/2010 | Morein et al. |
| 9,205,147 B2 | 12/2015 | Morein et al. |
| 2002/0041895 A1 | 4/2002 | Gregoriadis |
| 2008/0095795 A1 | 4/2008 | Morein et al. |
| 2011/0081378 A1 | 4/2011 | Morein |
| 2014/0120131 A1 | 5/2014 | Morein et al. |
| 2016/0114034 A1* | 4/2016 | Morein ................ A61K 39/39 424/209.1 |

FOREIGN PATENT DOCUMENTS

| | | |
|---|---|---|
| EP | 0415794 A1 | 3/1991 |
| WO | WO 92/06710 A1 | 4/1992 |
| WO | WO 96/11711 A1 | 4/1996 |
| WO | WO 2004/030696 A2 | 4/2004 |

OTHER PUBLICATIONS

Chappuis (Veterinary Microbiology. 1995; 44: 351-358).*
De Vries et al. (Journal of Virology. 1988; 69: 2071-2083).*
A. Eichhorn et al., "The Behavior of *Brucella abortus* Vaccine in Various Excipients," American Journal of Veterinary Research, 1(1): 3-17, dated Oct. 1940.
Albert Bendelac et al., "Adjuvants of Immunity: Harnessing Innate Immunity to Promote Adaptive Immunity," J. Exp. Med., 195(5): pp. F19-F23, dated Mar. 4, 2002.
B.A. Vanselow et al. "Field trials of ephemeral fever vaccines" Veterinary Microbiology, 46: 117-130, dated Mar. 8, 1995.
B.A. Vanselow et al., "A bovine ephemeral fever vaccine incorporating adjuvant Quil A: A comparative study using adjuvants Quil A, aluminium hydroxide gel and dextran sulphate," The Veterinary Record, 117: 37-43, dated Jul. 13, 1985.
Barr, Ian G., et al., ISCOMs (immunostimulating complexes): The first decade; CSL Limited, Parkville, Victoria, Australia; Immunology and Cell Biology (Feb. 1996) vol. 74, pp. 8-25.
BCCDC Laboratory Services; A Guide to Selection and Use of Disinfectants; BC Centre for Disease Control, 2003, pp. 1-18.
Behboudi, S., Morein, B. and Villacres-Eriksson, M.C., "Quillaja Saponin Formulations that Stimulate Proinflammatory Cytokines Elicit a Potent Acquired Cell-Mediated Immunity," Scand J. lmmunol., 50, 1999, 371-377.
Bengt Ronnberg et al., "Adjuvant activity of non-toxic Quillaja saponaria Molina components for use in ISCOM matrix," Vaccine, 13(14): 075-1382, dated 1995.
Bror Morein et al. "Immunomodulation by Iscoms, Immune Stimulating Complexes," Methods, 19:94-102, dated Aug. 33, 1999.
Bror Morein et al., Declaration under 37 CFR 1.132 submitted in U.S. Appl. No. 10/550,026, "Composition Comprising ISCOM Particles and Live Micro-organisms," pp. 1-13, exhibit A (two pages), and exhibit B (one page), dated Apr. 11, 2009.
Carl J. Burke et al., "Formulation, Stability, and Delivery of Live Attenuated Vaccines for Human Use," Critical Reviews in Therapeutic Drug Carrier Systems, 16(1): 1-83, dated 1999.

(Continued)

*Primary Examiner* — Shanon A. Foley
(74) *Attorney, Agent, or Firm* — Cooley LLP

(57) ABSTRACT

Iscom particles can be used as an adjuvant for preparing of an antigenic composition which comprises live micro-organisms and/or killed micro-organisms and/or antigenic molecules. A composition may comprise at least one iscom particle and one or more live micro-organisms and/or killed micro-organisms and/or antigenic molecules. A kit can comprise at least one compartment containing at least one living organism and at least one compartment containing at least one iscom particle.

23 Claims, No Drawings

(56) References Cited

OTHER PUBLICATIONS

Chavali S., et al., Adjuvant Effects of Orally Administered Saponins on Humoral and Cellular Immune Responses in Mice; Immunobiol., vol. 174, Mar. 2, 1987, pp. 347-359.

Chavali S., et al., An In Vitro Study of Immunomodulatory Effects of Some Saponins; International Society for Immunopharmacology, vol. 9, No. 6, Mar. 24, 1987, Great Britain, pp. 675-683.

Choi. et al., The level of protection against rotavirus shedding in mice following immunization with a chimeric VP6 protein is dependent on the route and the coadministered adjuvant, Vaccine 20 (Mar. 2002) 1733-1740, Elsevier Science Ltd.

Communication pursuant to Article 94(3) EPC issued in European Patent Application No. 04 712 123.8, four pages, dated Jun. 26, 2008.

Communication pursuant to Article 94(3) EPC issued in European Patent Application No. 04 712 123.8, four pages, dated Feb. 5, 2010.

Communication pursuant to Article 96(2) EPC issued in European Patent Application No. 04 723 123.8, four pages, dated Jul. 26, 2007.

Communication pursuant to Article 96(2)EPC issued in European Patent Office Application No. 04 723 123.8-2402, four pages, dated Dec. 27, 2006.

Communication under Rule 71(3) EPC issued in European Patent Application No. 04 712 123.8, thirty-four pages, dated Sep. 16, 2011.

Data analysis filed by patentee Isconova in Request to reject opposition against EP1635867, pp. 1-4, dated Apr. 23, 2013.

Decision to grant a European patent pursuant to Article 97(1) EPC issued in European Patent Application No. 04 712 123.8, one page, dated Jan. 12, 2012.

Dexiang Chen et al., "Opportunities and challenges of developing thermostable vaccines," Expert Rev. Vaccines 8(5): 547-557, dated 2009.

F. Bozic et al., "Levamisole mucosal adjuvant activity for a live attenuated *Escherichia coli* oral vaccine in weaned pigs," J. Vet. Pharmacol. Therap. 26: 225-231, dated Nov. 29, 2002.

Fohlman, Jan et al., Vaccination of Balb/c mice against enteroviral mediated myocarditis; Vaccine, vol. 8, Aug. 1990; Butterworth-Heinemann Ltd; pp. 381-384.

Francis, George, et al., The Biological Action of Saponins in Animal Systems: A Review; British Journal of Nutrition (Dec. 2002), vol. 88, pp. 587-605; The Authors 2002.

Gideon F.A. Kersten et al., "On the structure of immune-stimulating saponin-lipid complexes (iscoms)," Biochimica et Biophysica Acta, 1062: 165-171, dated 1991.

Gupta et al., "Adjuvants—a balance between toxicity and adjuvanticity," Vaccine, vol. 11 No. 3, pp. 293-306 (1993).

Harold F. Stills, Jr., 2005, "Adjuvants and Antibody Production: Dispelling the Myths Associated with Freund's complete and Other Adjuvants," ILAR Journal, vol. 46, Issue 3, pp. 280-293.

Hu, Ke-Fei et al., Immunostimulating Complexes (ISCOMs) for Nasal Vaccination; Elsevier Science B.V. Advanced Drug Delivery Reviews 51 (2001) pp. 149-159.

Incorporation and iscom—PubMed Results; http://www.ncbi.nlm.nih.gov/sites/entrez, Jun. 14, 2009, pp. 1-3.

Incorporation and live iscom—PubMed Results; http://www.ncbi.nlm.nih.gov/sites/entrez; Jun. 14, 2009, pp. 1-16.

Information regarding revocation of EP1635867, oral proceedings on Dec. 6, 2013 issued in European Patent Application No. 04 712 123.8, one page, dated Dec. 6, 2013.

Initiative for Vaccine Research, Live Attenuated Vaccines; World Health Organization, Jun. 2009, p. 1.

Invitation pursuant to Article 94(3) and Rule 71 (1) EPC issued in European Patent Application No. 04 712 123.8, three pages, dated May 30, 2011.

Iosef, et al., Systemic and Intenstinal Antibody Screening Cell Responses and Protection in Gnotobiotic Pigs Immunized Orally With Attenuated WA Human Rota Virus and WA 2/6-Rotav Irus-Like-Particles Associated With Immunostimulating Complexes, Vaccine 20 (Mar. 2002) 1741-1753.

Iscom—PubMed Results; http://www.ncbi.nlm.nih.gov/sites/entrez, Jun. 14, 2009, pp. 1-3.

ISCOM Technology Platform, Isconova, http://www.isconova/technology.aspx; dated Oct. 31, 2012.

Jack Cameron, "Anthrax: the disease in relation to vaccines," Vaccine, 2: 237, dated Dec. 1984.

Janeway, C.A., Travers, P., Walport, M.J., and Shlomchik, M.J., Immune Biology the Immune System in Health and Disease, Garland Publishing, New York, NY, 2001, Chapter 1—Basic Concepts in Immunology, 1-34.

Janeway, C.A., Travers, P., Walport, M.J., and Shlomchik, M.J., Immune Biology the Immune System in Health and Disease, Garland Publishing, New York, NY, 2001, Chapter 2—Innate Immunity, 35-91.

Janeway, C.A., Travers, P., Walport, M.J., and Shlomchik, M.J., Immune Biology the Immune System in Health and Disease, Garland Publishing, New York, NY, 2001, Chapter 14—Manipulation of the Immune Response, 553-596.

Janeway, C.A., Travers, P., Walport, M.J., and Shlomchik, M.J., Immune Biology the Immune System in Health and Disease, Garland Publishing, New York, NY, 2001, Afterword—Evolution of the Immune System: Past, Present, and Future, by Charles A.Janeway, Jr., 597-611.

K. Dalsgaard, "Thin-layer chromatographic fingerprinting of commercially available saponins," Dansk Tidsskr., 44: 327-331, dated Jun. 16, 1970.

Karen Burke, Glynis Dunn, Morag Ferguson, Philip D. Minor, & Jeffrey W. Alamond, "Antigen Chimaeras ofpoliovirus as Potential New Vaccines", Nature, vol. 332, Mar. 1988. (Abastract Only), pp. 1-2.

Karin Lovgren-Bengtsson et al., "The ISCOM Technology," Methods in Molecular Medicine, vol. 42: Vaccine Adjuvants: Preparation Methods and Research Protocols, pp. 239-258, dated Apr. 2000.

Lipford et al., "Vaccination with immunodominant peptides encapsulated in Quil A-containing liposomes induces peptide-specific primary CD8+ cytotoxic T cells," Vaccine, vol. 12 No. 1, pp. 73-80 (Jan. 1994).

Maria S. Di Genaro et al, Apr. 2003, "Attenuated Yersinia enterocolitica Mutant Strains Exhibit Differential Virulence in Cytokine-Deficient Mice: Implications for the Development of Novel Live Carrier Vaccines," Infection and Immunity, American Society of Microbiology, vol. 71, Issue 4, pp. 1804-1812.

Marshall, B. G., Wangoo, A., O'Gaora, P., Cook, H.T., Shaw, R.J., and Young, D.B., "Enhanced Antimycobacterial Response to Recombinant *Mycobacterium bovis* BCG Expressing Latency-Associated Peptide," Infection and Immunity, vol. 69, No. 11, Nov. 2001, 6676-6682.

Max Sterne et al., "The Use of Saponin Spore Vaccine for Inoculation against Anthrax in South Africa" Onderstepoort Journal of Veterinary Science and Animal Industry. 12(2): 279-301, dated Apr. 1939.

McNeal et al. "Stimulation of Local Immunity and Protection in Mice by Intramuscular Immunization with Triple- or Double-Layered Rotavirus Particles and QS-21" Viroloogy; 243,158-166 dated Jan. 27, 1998.

McNeal, et al., Antibody responses and protection stimulated by sequential oral-parenteral immunization of mice with rotavirus, Vaccine 17 (Feb. 1999) 639-645, Elsevier Science Ltd.

Mooij. P., Nieuwenhuis, I.G., Knoop, C.J., Dams, R.W., Bogers, W.M.J.M., Haaft, P.J.F., Niphuis, H. Koornstra W. Bieler, K., Kastler, J., Morein, B., Cafaro, A., Ensoli, B., Wagner, R., and Heeney, J.L., "Qualitative T-Helper Responses to Multiple Viral Antigens Correlate with Vaccine-Induced Immunity to Simian/Human Immunodeficiency Virus Infection," Journal of Virology, vol. 78, No. 7, Apr. 2004, 3333-3342.

Morein, B, et al.; Iscom, A Novel Structure for Antigenic Presentation of Membrane Proteins from Enveloped Viruses; Nature, vol. 308, No. 5958, Mar. 29, 1984; reprinted from pp. 457-460; Macmillan Journals Ltd., 1984, pp. 1-3.

Notice of opposition to a European patent issued in European Patent Application No. 04 712 123.8, twenty-one pages, dated Nov. 8, 2012.

(56) References Cited

OTHER PUBLICATIONS

P. Roy et al., "Potentiation of Immune Response of Live Lentogenic Newcastle Disease Vaccine using Adjuvant," Tropical Animal Health and Production, 30: 37-39, dated 1998.
P.G.W. Plagemann, "Hepatitis C Virus", Jun. 4, 1991, Arch Viral, vol. 120, pp. 165-180.
Peter C.B. Turnbull. "Anthrax vaccines: past, present and future," Vaccine, 9: 533-539, dated Aug. 1991.
Peter Hambleton et al., "Anthrax: the disease in relation to vaccines," Vaccine, 2: p. 125 and p. 127, dated Jun. 1984.
Pierre Tiollais, Christine Pourcel & Anne Dejean, "The Hepatitis B Virus", Oct. 10, 1985, Nature, vol. 317, pp. 489-495.
Pyle, S.W., Morein, B., Bess, J.W., Akerblom, L., Nara, P.L., Nigida, S.M., Lerche, N.W., Robey, W.G., Fischinger, P.J., and Arthur, L.O., "Immune Response to Immunostimulatory Complexes (ISCOMS) Prepared from Human Immunodeficiency Virus Type 1 (HIV-1) or the HIV-1 External Envelope Glycoprotein (gp120)," Vaccine, vol. 7, 1989, 465-473.
Rajput, Zahid Iqbal et al., Adjuvant Effects of Saponins on Animal Immune Responses; Journal of Zhejiang University Science B, 2007 vol. 8 (3) pp. 153-161.
Reply to communication in European Patent Application No. 04 723 123.8, eight pages, dated Jun. 26, 2007.
Response to communication dated Jul. 29, 2013, six pages, dated Oct. 7, 2013.
Response to communication pursuant to Article 94(3) EPC issued in European Patent Application No. 04 712 123.8, six pages, dated Oct. 6, 2008.
Response to Invitation pursuant to Article 94(3) and Rule 71 (1) EPC issued in European Patent Application No. 04 712 123.8, ten pages, dated Jun. 16, 2011.
Response to Official action dated Feb. 5, 2010 issued in European Patent Application No. 04 712 123.8, ten pages, dated Jul. 13, 2010.
Response to Official action dated Jul. 26, 2007 in European Patent Application No. 04 712 123.8, six pages, dated Jan. 28, 2008.
Response to opposition issued in European Patent Application No. 04 712 123.8, twenty-six pages, dated Apr. 23, 2013.
Roner, Michael R., et al., Antiviral Activity Obtained from Aqueous Extracts of the Chilean Soapbark Tree (Quillaja Saponaria Molina); Journal of General Virology, Jan. 2007, vol. 88, pp. 275-285.
Rosemary E. Smith et al, May 1999, "Immune-Stimulating Complexes Induce an IL-12 Dependent Cascade of Innate Immune Responses," The Journal of Immunology, 162, pp. 5536-5546.
S. Rao Chavali et al., "Immunomodulator Effects of Orally-Administered Saponins and Nonspecific Resistance against Rabies Infection," Int. Archs Allergy Appl. Immun., 84: 129-134, dated 1987.
Sai Saraswathi V. et al., "A Sin of Biotechnology, Bioterrorism-Anthrax," International Journal of PharmTech Research, 2(3): 2044-2047 dated Jul.-Sep. 2010.
SIGMA Product Information; techserv@sial.com; Saponin From Quillaja Bark Purified; Sigma Prod. No. S4521; Case No. 8047-15-2; Oct. 25, 1996; pp. 1-3.
Sjolander et al. "ISCOMs: and adjuvant with multiple functions" Journal of Leukocyte Biology, 64: 713-723 dated Dec. 1998.
Sjolander et al. 2001. "Intranasal immunisation with influenza—ISCOM induces strong mucosal as well as systemic antibody and cytotoxic T-lymphocyte." Vaccine vol. 19(28-29), Jul. 16, 2001, pp. 4072-4080.
Sjolander, A. Bengtsson, K.L., Johansson, M. and Morein, B., "Kinetics, Localization and Isotype Profile of Antibody Responses to Immune Stimulating Complexes (Iscoms) Containing Human Influenza Virus Envelope Glycoproteins," Scand. J. Immunol. 43, 1996, 164-172.
Sjolander, A., Bengtsson, K.L., and Morein, B., "Kinetics, Localization and Cytokine Profile of T Cell Responses to Immune Stimulating Complexes (iscoms) Containing Human Influenza Virus Envelope Glycoproteins," Vaccine, vol. 15, No. 9, 1997, 1030-1038.

Sjolander, A., Land, B.V., and Bengtsson, K.L., "Iscoms Containing Purified Quillaja Saponins Upregulate both Th1- like and Th2-like Immune Responses," Cellular Immunology, 177, 1997, 69-76.
Smith, R.E., Donachie, A.M., and Mel Mowat, A., "Immune Stimulating Complexes as Mucosal Vaccines," Immunology and Cell Biology, 76, 1998, 263-269.
Soren Kamstrup et al., "Preparation and characterisation of quillaja saponin with less heterogeneity than Quil-A," Vaccine, 18: 2244-2249, dated 2000.
Sparg, S.G., et al. Biological Activities and Distribution of Plant Saponins; Journal of Ethno-Pharmacology; www. elsevier.com/locate/jethpharm; vol. 94 (Oct. 2004), pp. 219-243.
Statistical analysis of data from Example 4, Annex 1, submitted in Opposition against EP1635867, one page, dated Aug. 11, 2012.
Stittelaar et al 2002, Longevity of neutralizing antibody levels in macaques vaccinated with Quil A-adjuvanted measles vaccine candidates. "Vaccine" vol. 21(3-4), Dec. 13, 2002, pp. 155-157, Available online Sep. 27, 2002.
Submission further to written submissions dated Oct. 7, 2013, one page, dated Nov. 4, 2013.
Submission regarding Oral Proceedings Scheduled Dec. 6, 2013 submitted in European Patent Application No. 04 712 123.8, eight pages, dated Dec. 3, 2013.
Summons to attend oral proceedings pursuant to Rule 115(1) EPC and preliminary opinion issued in European Patent Application No. 04 712 123.8, fourteen pages, dated Jul. 29, 2013.
Takahashi, Hidemi et al.; Induction of CD8 Cytotoxic T cells by Immunization with Purified HIV-1 Envelope Protein in ISCOMs; Nature, vol. 344, Apr. 26, 1990; pp. 873-875.
The European Agency for the Evaluation of Medicinal Products, Human Medicines Evaluation Unit; Committee for Proprietary Medicinal Products, Note for Guidance on Pharmaceutical and Biological Aspects of Combined Vaccines; London, Jul. 23, 1998 pp. 1-14.
The European Medicines Agency, Evaluation of Medicines for Human Use; Committee for Medicinal Products for Human Use, Guideline on Adjuvants in Vaccines for Human Use; London, Jan. 20, 2005, pp. 1-18.
Vaccine Development Overview; http://www.brown.edu/Courses/Bio_160/Projects1999/vaccineoverview, Jun. 16, 2009; pp. 1-5.
van Binnendijk et al, 1997. Protective immunity in Macaques vaccinated with live attenuated recombinant and subunit vaccines in the presence of passively acquired antibodies. "J. Infect Diseases" vol. 175, pp. 524-532.
Van Rooij et al., "Analysis of protective immunity against PRV infection in pigs using attenuated and inactivated PRV vaccines," Vet. Res., 31: 135, dated 2000.
Vancott, et al., Mice Develop Effective but Delayed Protective Immune Responses When Immunized as Neonates either intranasally with Nonliving VP6/L T (R192G) or Orally with Live Rhesus Rotavirus Vaccine Candidates, Journal of Virology, May 2006 pp. 4949-4961, American Society for Microbiology.
Viruses, Bacterial and Fungi, Sizes and Significance; Ion Life, http://www.ionizers.org; Jun. 16, 2009, pp. 1-4.
Ward, et al., VP6: A Candidate Rotavirus Vaccine, The Journal of Infectious Diseases, Sep. 2010, 202 (S1): S101-S107, The Infection Diseases Society of America.
Written submission in preparation for the oral proceedings (Rule 116 EPC) issued in European Patent Application No. 04 712 123.8, twenty-four pages, dated Oct. 7, 2013.
www.patentstorm.us/patents/6177081/description.html; Human and Marmoset Activation Viruses—U.S. Pat. No. 6177081. Jun. 16, 2009. p. 1.
Yifan Zhan et al., Aug. 1998, "Control of IL-12 and IFN-γ Production in Response to Live or Dead Bacteria by TNF and Other Factors," The Journal of Immunology, 161, pp. 1447-1453.
Yuan et al., "Protective Immunity and Antibody-Secreting Cell Responses Elicited by Combined Oral Atenuated WA Human Rota Virus and Intranasal WA 2/6-VLPS With Mutant *Escherichia coli* Heat-Labile Toxin in Gnotobiotic Pigs", J. of Virology, 75(19), Oct. 2001, 9229-9238.

\* cited by examiner

COMPOSITIONS COMPRISING ISCOM PARTICLES AND LIVE MICRO-ORGANISMS

CROSS-REFERENCE TO RELATED APPLICATIONS

This application is a continuation of application Ser. No. 14/146,365, filed Jan. 2, 2014, which is a continuation of application Ser. No. 12/905,418, filed Oct. 15, 2010, which is a divisional of application Ser. No. 10/550,026, filed Jun. 11, 2007, now U.S. Pat. No. 7,838,019, which is a national stage application of International Application PCT/SE04/000451, filed in English on Mar. 24, 2004 and which claims priority of Swedish patent application No. 0300795-2, filed Mar. 24, 2003, all of which are hereby incorporated by reference.

The present invention relates to the use of iscom particles as adjuvant for preparing of an antigenic composition, which comprises live micro-organisms and a composition comprising at least one iscom particle and one or more living micro-organisms.

TECHNICAL BACKGROUND

Today adjuvants are used to enhance the immunogenicity of antigens which are not replicating i.e. in so-called killed or inactivated vaccines. Although, many vaccines contain several kinds of vaccine antigens in order to cover immune protection against several infectious diseases live and killed vaccine antigens are not mixed. One reason for that is that killed vaccines need adjuvant to enhance the efficacy of killed vaccines.

Live vaccines contain micro-organisms that replicate in the host i.e. the live attenuated vaccine antigens which are micro-organisms that are closely related to the pathogen i.e. the micro-organisms that cause disease. Thus, the host is producing most of the vaccine antigens when replicating vaccine antigens are used resulting in in vivo production of high doses of vaccine antigens in the host.

Moreover, the production of vaccine antigens in the host over a period of time contributes also to make the live vaccines effective, and even one administration of an efficient live vaccine often suffices to evoke long lasting immune protection. For certain pathogens there is no live properly attenuated micro-organism available to present them in a vaccine, either because the attenuation is not achieved, or that after the attenuation the micro-organism does not induce a potent immune protection.

There are both practical and economical reasons to give the vaccine antigens in one or as few administrations as possible, when there is a defined period for vaccination. Such a period is in the early childhood respectively newborn animals when a vaccine for protection against up to seven different infectious diseases are given in one injection. Another period is when a large number of animals are gathered in e.g. fattening units form different farms and regions. Still another such a period is before travel to exotic countries to induce immune protection against exotic infectious diseases, i.e. pathogens that are not present in the home country.

Most vaccines for dogs are used in puppies and the first vaccination is carried out just before or at the time for delivery to the new owner. There is a strong tendency, not to say desire, to avoid more than one primary administration of vaccine and limit the number of re-vaccinations. Most vaccines in dogs are live and killed vaccine antigens are avoided in multicomponent dog and cat vaccines, mainly due to the fact of the difficulty to combine live and killed vaccines. Thus a dog vaccine today is mostly a live multi-component vaccine (and) composed to protect against up to seven different infectious diseases.

A frequently used killed vaccine for dog and cat is the rabies virus vaccine. *Bordetella bronchiseptica* (Bb) is also desired as a killed vaccine, since the live vaccine causes side effects. A killed Bb component vaccine (sub unit) would need adjuvant supplementation. These vaccines are single component vaccines. The killed Rabies virus vaccine requires adjuvant, and so far aluminium hydroxide is used, which adsorbs the micro-organisms and interferes thereby with their replication.

In cat, the feline leukemia virus is a killed vaccine (sub unit) based on gp70, being a surface protein of the virus. Also this vaccine antigen requires adjuvant. The present used adjuvant formulation is composed of free saponin (QS21) and Al(OH)3, a mixture that will lyse viral membranes and kill the virus. The Al(OH)3 component causes in rare cases fibrosarcoma, conceived to be caused by the depot effects of some adjuvants e.g., oil or Al(OH)3 (report from the Veterinary Products Committee Working Group on Feline and Canine Vaccination Department for Environment, Food & Rural Affairs (DEFRA) Publications Admail 6000 London SWIA2XX).

Thus, there is a desire to be able to use killed and live vaccines mixed in a common formulation and that they should be compatible with each other in the formulation. Further an adjuvant present in a vaccine formulation must not cause adverse side effects.

It has now surprisingly turned out that iscoms and iscom matrix particles can be used as adjuvants for killed vaccine antigens e.g. in a multi component vaccine without causing negative effects on the live replicating vaccine components. This is contrary to most (other) commonly used adjuvants that decrease the capacity of the live microorganisms to replicate.

Unexpectedly, the iscom/iscom-matrix adjuvant was not only harmless to the live components, it also enhanced the immune response against the live vaccine components.

SUMMARY OF THE INVENTION

The present invention relates to the use of iscom particle(s) as adjuvant in a formulation of vaccine antigens, which comprise at least one iscom—iscom matrix particle together with a non-replicating vaccine antigen and one or more living micro-organisms.

Several saponins formulated in iscom and iscom matrix have been tested for their effect on various viruses, which are involved in vaccine formulations. Live vaccine antigens were mixed with the adjuvant formulation and the mixture incubated for two or more hours. Thereafter, the capacity of the micro-organism to replicate in cell cultures or in a host, in this case in a chicken embryo, was measured. The iscom particles did not hamper the replication of the live micro-organisms and even enhanced proliferation contrary to several other commonly used adjuvants, that were tested.

DETAILED DESCRIPTION OF THE INVENTION

The present invention relates to the use of an iscom or iscom matrix particle as adjuvant together with one or more non-replicating i.e. killed vaccine antigen(s) in an antigenic composition, which comprises at least one type of live micro-organism. The killed vaccine antigen may also include virus and bacteria (vectors) that contain foreign antigen(s) of interest for prophylaxes and therapy expressed by inserted genes in the vector.

By live micro-organism we understand a micro-organism that can replicate in the host. The live micro-organism must not be in a condition to cause adverse reactions in the host. Therefore, preferably attenuated micro-organisms are used. Attenuation is known in the art and may be performed as described in New Vaccine Technologies (2001) Ed. Ronald W Ellis, Landes Bioscience, Georgetown, Tex., USA.

The live i.e. replicating micro-organism may be any micro-organism of interest for use as an antigen for triggering or modulating the immune system. It also includes virus and bacteria (vectors) that contain foreign antigen(s) of interest for prophylaxes and therapy expressed by inserted genes in the vector. The micro-organisms may be chosen from viruses including smallpox virus, Japanese encephalitis virus, yellow fever vaccines, poliovirus vaccines, measles vaccines, rubella vaccines, mumps vaccines and trivalent vaccines including measles, mumps-rubella vaccines or even one more live virus vaccine i.e. varicella vaccine; gram+ and gram– live bacterial vaccines including live attenuated *mycobacterium bovis* (BCG Tuberculosis Vaccine), live attenuated *Salmonella typhi*, live attenuated *Shigella* spp, live virulence-attenuated *vibrio cholerae*, pediatric. An example of an adeno vector is a vaccine expressing a tumor antigen p53 registered for therapy of head and neck squamous carcinoma. In clinical trials is a cervical cancer vaccine where the antigen is expressed by a vaccinia virus (modified vaccinia Ankara/MVA/) (Nature Biotechnology Vol 22 No 1 January 2004). Examples of live vaccines in animals, but not limited to the examples, are vaccines against Canine distemper virus, Canine parvovirus, Canine adenovirus, *Bordetella bronchiseptica* virus, Parainfluenza 3 viruses in dogs and cattle, Feline parvovirus such as Feline panleukopenia virus, Feline calici virus, Feline herpesvirus and Feline *Chlamydia psittaci* virus. Examples of replicating vector vaccine for cat is feline leukemia virus vaccine, in which the surface protein gp70 of the virus is expressed by a canarypox virus (ALVAC) and the poultry vaccines against Marek's disease where the vaccine antigen is expressed by the ALVAC vector and the vaccine against infectious bursa disease virus for which also the ALVAC vector is used. One purpose of the invention is to raise the vaccine effect of live, preferably attenuated micro-organisms.

At present killed and live (replicating) vaccines are often not presented in the same vaccine formulation. In the cases when live and non-replicating (killed) vaccine antigens are used there is today no adjuvant component.

Therefore, another purpose of the invention is to provide a composition where live possibly attenuated micro-organisms are mixed with killed micro-organisms and an adjuvant.

Thus, the iscom particles may also be used in a composition that further comprises at least one killed or inactivated micro-organism together with one or more live microorganisms. Inactivation is known in the art and may be performed as described in New Vaccine Technologies (2001) Ed. Ronald W Ellis, Landes Bioscience, Georgetown, Tex., USA or as described by Rueda. P. et al. 2001. Vaccine 19 (2001) p. 726-734. Effect of different baculovirus inactivation procedures on the integrity and immunogenicity of Porcine Parvo virus-like particles.

Different species of micro-organisms may be used in the same composition comprising the iscom particles or in different compositions for co-administration at the same event.

The invention also relates to the use of the iscom particles together with live microorganisms in a vaccine composition for eliciting an immune protection in a host treated with the vaccine. Live attenuated vaccines are sometimes overattenuated and thus poorly immunogenic and it is of great interest to improve the immunogenicity also of the live vaccine components.

Inactivated bacterial vaccines that include conjugate or sub-unit vaccines such as group Streptococci, group A Streptococci, *Haemophilus influenzae, Neisseria meningitides, Bordetella pertussis, Streptococcus pneumonia, Mycoplasma* pneumonia. Examples of adult attenuated vaccines are those against cholera, enterotoxic *E. coli*, shigellosis, etc.

Killed vaccines, but not limited to the examples are, for use in animals (dogs) parvovirus vaccine, rabies virus vaccines, vaccines against leptospirosis such as *Leptospira canicola, Leptospira icterohaemorrhagiae* and vaccine against respiratory syncytial and bovine virus diarrhoea virus, bovine herpes virus 1 in cattle, or influenza viruses in horse. For cats there are Feline panleukopenia (parvo) virus vaccine, Feline calici virus vaccine, Feline herpesvirus vaccine, Feline *Chlamydia psittaci* vaccine, Feline leukemia virus (FeLV) vaccine and Feline rabies vaccine.

Examples of killed vaccines for use in humans are inactivated virus vaccines include tick-borne encephalitis-, rabies-, hepatitis A-, polio-, influenza viruses.

The invention may be used with any killed or live preferably attenuated micro-organism for any species and the above mentioned examples do not limit the scope of the invention.

The invention also relates to the use of iscom particles whereby the antigenic composition further comprises one or more antigenic molecules.

The iscom particle may be an iscom or an iscom matrix particle or any sub-fragment thereof.

Iscom contains at least one glycoside, at least one lipid, and at least one kind of antigen substance or epitope. These substances may be of different kind such as proteins and peptides, glycoproteins and glycopeptides, carbohydrates etc. These complexes enhance the immunogenicity of the included antigens and may also contain one or more immunomodulatory (adjuvant-active) substances. Iscoms may be prepared as described in EP 0 109 942 BI, EP 0 242 380 BI and EP 0 180 546 B1.

Matrix contains at least one glycoside, which is an adjuvant-active substance and at least one lipid. Matrix has an immunoenhancing effect on co-administered antigenic substances, see EP 0 436 620 B1. Matrix may contain other immunostimulating and enhancing components than saponins e.g. lipopolysaccharides (LPS), Lipid A or Lipid A derivatives, CT or LT and their sub-fragments or derivatives thereof e.g., LTB, LTA, CTB, CTA or CTA 1-DD.

Iscom particles containing such antigenic molecules integrated into the particle, coupled on to the particle or simply mixed into the composition may be used together with the live and/or inactivated micro-organisms.

The lipids used are particularly those described in the applicant's patent EP 0 109 942 B1 in particular on p. 3 and in patent EP 0 436 620 B1 on p. 7 lines 7-24. Especially sterols such as cholesterol and phospholipids such as phosphatidylethanolamine and phosphatidylcholine are used. Lipid-containing receptors that bind to the cell-binding components, such as glycolipids including the cholera toxin's receptor, which is the ganglioside GM1, and fucosed blood group antigen may be used. The cell-binding components can then function as mucus targeting molecule and be bound to the lipid-containing substances through simply mixing them with complexes that contain them. Iscom complexes comprising such receptors and receptors are described in WO 97/30728.

The glycoside in the iscom particles may be any glycoside. Preferred glucosides are described in EP 0 109 924 B1. Especially preferred are raw extract from *Quillaja Saponaria* Molina (Dalsgaard, K. (1974), Arch. Gesamte Virusforsch, 44, 243.), or any subfraction thereof as described in PCT/US/88101842 to Kensil et al., Kensil, C. A. et al. (1991), J. Immunol., 146, 431, Kersten, G. F. A. et al. (1990). "Aspects of Iscoms. Analytical, Pharmaceutical and Adjuvant Properties; Thesis, University of Utrecht, EP 0 362 279 B2 and EP 0 555 276 B1.

The saponin fractions according to the invention may be the A, B and C fractions described in WO 96/11711, the B3, B4 and B4b fractions described in EP 0 436 620, and the fractions QA1-22 described in EP 0 362 279 B2, Q-VAC (Nor-Feed, AS Denmark), *Quillaja Saponaria* Molina Spikoside (Isconova AB, Uppsala Science Park, 751 83, Uppsala, Sweden).

The fractions QA-1-2-3-4-5-6-7-8-9-10-11-12-13-14-15-16-17-18-19-20-21 and 22 of EP 0 362 279 B2, Especially QA-7, 17-18 and 21 may be used. They are obtained as described in EP 0 363 279 B2, especially at page 6 and in Example 1 on, page 8 and 9.

Preferably sub fractions A and C are used. It has surprisingly turned out that A-matrix and C-matrix enhances virus growth (see Example 2).

The term "one saponin fraction from *Quillaja Saponaria* Molina" is used throughout this specification and in the claims as a generic description of a semi-purified or defined saponin fraction of *Quillaja Saponaria* or a substantially pure fraction. It is important that the fraction does not contain as much of any other fraction to negatively affect the good results that are obtained when the mixtures of iscom or iscom matrix comprising essentially one fraction is used. The saponin preparation may, if desired, include minor amounts for example up to 40% by weight, such as up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight, up to 0.1% by weight of other compounds such as other saponins or other adjuvant materials. The antigenic molecules may be coupled on to the iscom matrix particle or simply mixed into the composition and used together with the live and/or inactivated micro-organisms.

The antigenic molecules which may be incorporated into or associated with the iscom matrix in accordance with this invention may be any chemical entity which can induce an immune response in an individual such as (but not limited to) a human or other animal, including but not limited to a humoral and/or cell-mediated immune response to bacteria, viruses, mycoplasma or other micro-organisms. The specific immunogen can be a protein or peptide, a carbohydrate, polysaccharide, a lipopolysaccharide or a lipopeptide; or it can be a combination of any of these.

Particularly, the specific antigenic molecule can include a native protein or protein fragment, or a synthetic protein or protein fragment or peptide; it can include glycoprotein, glycopeptide, lipoprotein, lipopeptide, nucleoprotein, nucleopeptide; it can include a peptide-peptide conjugate; it can include a recombinant nucleic acid expression product.

Examples of such immunogens are cited in EP 0 109 942 B1 and include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, *haemophilus* influenza, *chlamydia*, varicella-zoster virus, rabies or human immunodeficiency virus.

Any type of iscom particle, iscom matrix particle, live and inactivated micro-organism and antigenic substance may be used together in a composition for use as an antigenic or immune modulating agent according to the invention.

Also, one or more iscom particles, iscom matrix particles, live and inactivated micro-organisms and antigenic substances may be used together in a composition for use as an antigenic or immune modulating agent according to the invention.

The invention also concerns a composition comprising at least one iscom particle and one or more living micro-organisms. The composition may be a vaccine, wherein the living micro-organism is a virus. Such a composition may further comprise one or more killed or inactivated micro-organisms. It may also comprise one or more antigenic molecules.

The composition may be used for animals within the veterinary medicine and for humans.

Pharmaceutical and veterinary medicine compositions according to the present invention, and for use in accordance with the present invention, may include, in addition to active ingredient, a pharmaceutically acceptable excipient, diluent, carrier, buffer, stabilizer, additive or other materials well known to those skilled in the art. Such materials should be non-toxic and should not interfere with the efficacy of the active ingredient. The precise nature of the carrier or other material will depend on the route of administration.

A live vaccine antigen is generally freeze dried and before administration the vaccine antigens (live micro-organisms) are dissolved in a pharmaceutically acceptable solvent. The solubilized, or suspended vaccine antigens shall immediately be administered to the individual. Before administration the freeze dried antigen is dissolved/suspended in a solvent that may contain the adjuvant i.e. iscom matrix or iscom formulation with or without the killed vaccine and/or antigenic substance(s). Alternatively before suspending/solubilizing of the freeze dried component in the vaccine the solvent is mixed with the iscom matrix and/or iscom particles and/or the killed micro-organisms and/or the antigenic molecules.

The pharmaceutically acceptable solvent may be a buffer e.g. PBS.

The live micro-organisms are preferably supplied freeze dried separate from the adjuvant particles.

Thus, the invention also relates to a kit of parts comprising at least one compartment containing at least one living organism and at least one compartment containing at least one iscom particle.

A kit of parts may comprise different compartments e.g. one or more compartments comprising at least one freeze dried live micro-organism and at least one compartment comprising at least one iscom particle. The iscom particle is preferably dissolved or suspended in a pharmaceutical acceptable solvent.

Another embodiment according to the invention relates to a kit of parts, which further comprises also at least one inactivated micro-organism, which may be present in a further compartment or in the same compartment as one compartment containing at least one iscom particle.

When antigenic molecules are present they may be integrated into or coupled on to an iscom particle or mixed with one or more iscom matrix particles and kept in the same compartment.

The amount of antigenic substance, inactivated micro-organism and live micro-organism is dependent on the substance and micro-organisms used and the individual to be treated. The content of live micro-organism further depends on the constitution of the micro-organism. For inactivated non living micro-organism in small animals the low dose is 0.1 μg up to 100 μg, for large animals the low dose range from 10 μg up to 300 μg that said not to be limiting borders. In humans the dose ranges are 1 μg up to 200 μg not being the limiting border.

The invention will now be further described byway of non-limiting examples. All references mentioned herein are incorporated by reference.

EXAMPLE 1

Preparation of Iscom-Matrix and ISCOMs

In the following experiments ISCOMs and Iscom-Matrix are used as vaccine adjuvant antigen delivery and adjuvant systems. Their capacity to enhance the immunogenicity of selected vaccine antigens are explored in the following experiments in formulations containing both killed vaccine antigens (non-replicating) and live vaccine antigens i.e. replicating. Useful formulations must both enhance the immunogenicity of the killed vaccine antigen and be compatible with the live vaccine antigen e. they must not reduce the replication and the immunogenicity of the live vaccine antigens. It would be beneficial if the ISCOMs and Iscom-Matrix also enhance the immunogenicity of the live vaccine antigens. In the following experiments these properties are explored in cell culture systems, in embryos and in an animal (mammal) model. The key to succeed with the formulations is that the potential negative properties of each constituent are not affecting the vaccine formulation negatively. E.g. the free *quillaja* saponin is very lytic and will lyse the enveloped virus used here and also the cells these viruses infect. Other adjuvants may have other negative effects e.g. by trapping the live vaccine antigen. This example describes the formulation of ISCOM and Iscom-Matrix, which neutralize and block negative effects of the free *quillaja* constituents.

Iscom-Matrix and ISCOMs were prepared as described in EP 0 109 942 BI, EP 0 242 380 B1, EP 0 180 546 B1 and EP 0 436 620 B1. A more detailed description of the specific examples in the present application is given below.

Materials
  Cholesterol, e.g., Sigma C8503 (USA)
  Phosphatidyl choline (egg derived) e.g., Lipoid E-PC (Germany)
  MEGA-10 (Bachem AG, Switzerland)
  Octyl glucoside (Bachem, Switzerland)
  *Quillaja* saponin Fraction A and C (patent W09611711)
  Semipurified saponin preparations, Spikoside (Isconova AB, Sweden) and Q-VAC (Norfeed AS, Denmark)
  0.22 μm Sterile filters (Acrodisc)
  PBS (10 mM phosphate buffered 150 mM saline, pH 6.8-7.4)
  Slide-A-Lyzer cassette MW cut off 12-14,000, Pierce (USA) 0.5-3 ml and 3-15 ml.

Virus
  Purified influenza virus A/PR/8/34 (H1N1), 6.0 mg/ml
  Purified bovine Respiratory syncytial virus (BRSV), 3.7 mg/ml MEGA-10 (Stock Solution)
  A 20% (w/w) stock solution was prepared by dissolving 2.0 g dry solid MEGA-10 in 8 ml distilled water, under gentle heating (30-50° C.). The solution was filtered through 0.22 μm sterile filter, divided in aliquots and stored at −20° C. until use.

Octyl Glucoside (Stock Solution)
  A 20% (w/w) stock solution was prepared by dissolving 2.0 g dry Octyl glucoside in 8 ml distilled water under gentle heating (30-50° C.). The solution was filtered through 0.22 um sterile filter, divided in aliquots and stored at −20° C. until use.

Lipid Mixture (15 mg/ml in MEGA-10)
  150 mg of each cholesterol and phosphatidyl choline was dissolved in 10 ml 20% MEGA-10, by gentle heating (30-60° C.) with slow stirring. The solution was filtered through 0.22 μl sterile filter, divided in aliquots and stored at −20° C. until use. Before use the frozen lipid mixtures was heated to 40-50° C. until clear.

Lipid Mixture (10 mg/ml in Octylglucoside)
  100 mg of each cholesterol and phosphatidyl choline was dissolved in 10 ml 20% Octylglucoside under gentle heating (30-60° C.) with slow stirring. The solution was filtered through 0.22 μm sterile filter, divided in aliquots and stored at −20° C. until use. Before use the frozen lipid mixtures were heated to 40-50° C. until the solution was clear.

Saponin Stock Solutions (100 mg/ml)
  1.0 gram of *Quillaja saponaria* Molina fractions A or C respectively or a mixture of 0.7 g A and 0.3 g C, Spikoside or Q-VAC was dissolved in 10.0 ml of distilled water. The solutions were filtered through 0.22 μm sterile filter, and the aliquots were stored at −20° C. until use.

The Iscom-Matrix preparations were produced as outlined in Table 1. The mixtures were prepared as follows using the MEGA-10 dissolved lipids;
  1. 2 ml PBS was added to a 50 ml Falcon tube
  2. the lipid mixture was added
  3. saponin was added and the mixture was mixed
  4. PBS was added up to a final volume of 12 ml
  5. the solution was mixed thoroughly and incubated at r.t.
  6. the solution was filled into Slide-A-Lyzer
  7. the solution was dialyzed against 4 changes of PBS (r.t. for 48-60 hours)
  8. the solution was aspirated from Slide-A-Lyzer and filtered through 0.22 m sterile filter.

TABLE 1

| Preparation (MATRIX) | Lipid mixture (15 mg/ml) | | Quillaja saponin (Frac A and/or C) | | PBS |
|---|---|---|---|---|---|
| | Amount (mg) | Volume (μl) | Amount (mg) | Volume (μl) | Volume (μl) |
| Matrix-A | 12 | 800 | 48* | 480 | 2.0 + 8.72 |
| Matrix-C | 12 | 800 | 30** | 300 | 2.0 + 8.90 |
| MB-703 | 12 | 800 | 42*** | 420 | 2.0 + 8.78 |
| Spikoside-Matrix | 12 | 800 | 60$^S$ | 600 | 2.0 + 8.60 |
| Q-VAC-Matrix | 12 | 800 | 120$^Q$ | 1200 | 2.0 + 8.00 |

*Fraction A alone
**Fraction C alone
***Fraction A + C mixture, consisting of 7 parts (mg) A + 3 parts (mg) C
$^S$Spikoside
$^Q$Q-VAC The formation of Iscom-Matrix was verified by negative staining electron microscopy and the resulting concentrations of saponin were determined by HPLC. (San Martin and Briones, Quality control of commercial *quillaja* (*Quillaja saponaria* Molina) extracts by reverse phase HPLC. *Journal of the Science of Food and Agriculture*, 80:2063-2068, 2000.

Matrix MM-703 was prepared by mixing 5.5 ml of Matrix-A with 3.0 ml of Matrix-C.

Preparation of PR8 (Influenza) and BRSV (Bovine Respiratory Syncytial Virus) ISCOMs Purified virus was (PR8 and BRSV respectively) were diluted in PBS to a concentration of 2.0 mg/ml.

The PR8 virus was solubilized by addition of MEGA-10 to a final concentration of 2% (w/w), the mixture was incubated for 30-60 min at r.t.

The BRSV virus was solubilized by addition of Octylglucoside to a final concentration of 1% (w/w), the mixture was incubated for 30-60 min at r.t.

The viral core was removed from the solubilized virus suspensions by ultracentrifugation and the supernatants containing the solubilized viral envelope glycoproteins were submitted for amino acid analysis prior to further incorporation into ISCOMs.

Per one mg of viral glycoproteins was added 1 mg of each cholesterol and phosphatidyl choline from the stock solutions (PR8/MEGA-10 and BRSV/Octyl glucoside) and 3.5 mg of Fraction A+C mixture (as described in Table 1 above) or 5 mg of Spikoside. The mixtures were incubated and filled into Slide-A-Lyzer cassettes (0.5-3 ml). The cassettes were dialyzed against 4 changes of PBS for 24-48 h at r.t. The formation of iscoms and incorporation of the viral glycoproteins was verified by electron microscopy and analytical sucrose-density gradient centrifugations as described before EP 0 109 942 BI.

EXAMPLE 2

ISCOM and Iscom Matrix Formulations do not Reduce the Virus Proliferation in Chicken Embryos in Contrast to the Conventionally Used Oil and Aluminium Hydroxide Adjuvants This example was carried out to explore the effect of various adjuvants on the replication of virus in chicken embryos. The negative effect can either depend on the effect of the respective adjuvants on the virus or on the cells being the target for virus infection.

The following adjuvant formulations were tested for their effect on live virus to explore if they would interfere with live virus antigen replication in the chicken embryo: A-matrix, C-matrix, 703-matrix, (MB703) crude Spikoside matrix, oil adjuvant (Freund's incomplete Adjuvant, aluminium hydroxide (Allhydrogel, Superfos AS), influenza virus iscoms and bovine respiratory syncytial virus iscoms. The Iscom and Iscom-Matrix preparations were prepared as described in EXAMPLE 1.

From a stock solution of influenza virus (allantoic fluid seed-virus), containing 10 log 9 a dilution in PBS 10 log 6 was prepared as working dilution. To one ml of this working virus dilution 50, 100 and 200 µg of each of the adjuvant formulations were added. The virus—adjuvant mixtures were incubated for at least 2 hrs at r.t. before 100 µl were injected into the allantoic fluid of 11 days embryonated hens eggs. The allantoic fluid was harvested at day 18 of hatch. The level of virus replication was measured as embryo infectious dose 50 (EID50) i.e. the end point where 50% of the embryos are infected. The detection of infection, i.e. the presence virus in the allantoic fluid from the embryonated egg, is based on the phenomenon that the influenza virus aggregates chicken red blood cells so-called hemagglutination (HA).

Results

Four control groups, which included 7 to 10 embryos each, were infected with influenza virus that was not pre-incubated with any of the adjuvant formulations. The EID50 titres ranged between 10 log 9.2 to 10 9.5.

None of the matrix or iscom formulations mentioned above reduced the EID50 titres compared to the EID50 titres measured in the control groups. In contrast oil and aluminium hydroxide reduced the EID50 titres more than a 10 log, which is unacceptable for blending with live vaccine antigens i.e. they can not be used in a vaccine containing live vaccine antigens (United States Pharmacopeia and National Formulary (USP-NF)). Thus, it is concluded that the matrix formulations are "compatible" for use in vaccines, which contain live micro-organisms.

EXAMPLE 3

Selected ISCOM and Iscom Matrix Formulations do not Reduce the Virus Replication in Cell Cultures in Contrast to Spikoside Matrix, Free Saponin C, Free 703 and Free Spikoside, Oil Adjuvant and Aluminium Hydroxide, which Decreased the Virus Proliferation Cell culture systems are sensitive in vitro systems for measuring virus replication. In this example the following adjuvant formulations were tested to explore if they interfered with the replication of various viruses. The following viruses were selected for the test because they are important targets for vaccines in various animal species: The indicator virus was canine distemper virus (CDV) in VERO cell cultures tested against A-matrix, C-matrix, 703 matrix (MB703), Spikoside matrix, Q-VAC matrix, oil adjuvant, aluminium hydroxide, free saponin A, free saponin C, free 703 and free spikoside, influenza virus iscoms and bovine respiratory syncytial virus iscoms. The Iscom and Iscom-Matrix preparations were prepared as described in EXAMPLE 1.

Methods

From a stock solution of CDV containing 10 log 5 a 10-fold dilution in virus medium without serum was prepared as working dilution. To one ml of this virus dilution 50, 100 and 200 µg of either of the adjuvant formulations was added. The virus-adjuvant mixtures were incubated for at least 2 hrs before 200 µl of the virus-adjuvant mixture in dilutions 10 log-1 (calculated from stock virus) to dilution 10 log-5 were allowed to adsorb for 1 to 2 hours at 37° C. to Vero cell cultures adherent to the 25 cm$^2$ plastic surface in Costar flasks (No. 3055, Corning Inc., Corning, N.Y. 14831, USA). Thereafter, virus suspensions respectively virus-adjuvant suspensions were removed as far as possible and cell culture medium containing 2% calf serum was added to each flask.

The level of virus replication was measured as tissue culture infectious dose 50 (TCID50), i.e. the end point where 50% of the tissue cultures are infected. The detection of infection, i.e. the presence virus in the tissue cultures is based on the cell destruction the virus is causing i.e. cytopathic effect (CPE). The specificity of the reaction was confirmed by immunofluorescence or by neutralization of recovered virus from the cell cultures. The cultures were followed and examined for 8 days when the virus controls showed 50 to 100% CPE (cell destruction), while uninfected cultures still had confluent layers of cells.

The virus controls included virus in the same dilutions treated in the same way as the virus-adjuvant mixtures, except that the virus suspensions were not mixed with the adjuvant formulations.

The cell controls were uninfected cells.

Each mixture and control assay was carried out in four replicates.

Results

The four virus controls, i.e. CDV that was not pre-incubated with any of the adjuvant formulations, titered out to 4.7 TCID50 10 LOG titres.

A-matrix, C-matrix treated virus titered both out to 5.7 i.e. a ten fold higher titre than the virus control i.e. an unexpected increase of virus growth.

703 matrix (4.7), A+C-matrix (4.7), Q-VAC matrix (4.5), free saponin A, influenza virus Iscoms (4.9) and bovine respiratory syncytial virus Iscoms (4.4). The titres in brackets show that all these formulations did not significantly differ from the titres of the virus control.

Spikoside matrix, free saponin C, free 703 and free spikoside, oil adjuvant and aluminium hydroxide decreased more than a ten fold the virus titres compared to the virus control.

Conclusion

Spikoside matrix, free saponin C, free 703 and free spikoside, oil adjuvant and aluminium hydroxide can not be used together with live vaccine antigens, because they decrease the capacity to replicate, when mixed with the live vaccine antigens (United States Pharmacopeia and National Formulary (USP-NF)).

703 matrix, A+C-matrix, Q-VAC matrix, free saponin A, influenza virus Iscoms and respiratory syncytial virus Iscoms can all be used as adjuvant in a vaccine containing vaccine components.

A-matrix, C-matrix treated enhanced virus growth in cell cultures an unexpected result, which can lead to increased efficacy.

EXAMPLE 4

Iscom-Matrix Strongly Enhances the Immunogenicity in Ferrets of a Killed Rabies Virus Vaccine not Hampering, Rather Enhancing the Immunogenicity of the Live Vaccine Components Included in the Vaccine In previous examples the effect of various adjuvants were tested for their effect on replication of live vaccine antigens in vitro in cell cultures and in vivo in chicken embryos. In this example the immunogenicity is analyzed in an animal (ferret) model using a commercial live multi-component vaccine. The intention was to demonstrate that an Iscom-Matrix formulation selected to enhance a killed rabies virus vaccine antigen has no negative effect on the immunogenicity of the live vaccine antigens included in the formulation. The live vaccine components were selected because they are commonly included in commercial vaccines for dog.

Experimental Layout

18 Ferrets were divided into three groups of 6 ferrets. Group 1 was vaccinated at week 0 with a commercial live vaccine (live attenuated vaccine against Canine Distemper, Adeno, Parvo and Parainfluenza virus) mixed with purified killed rabies virus component. At week 4, the Ferrets were boosted with the killed Rabies virus component.

Groups 2 and 3 were vaccinated at week 0 with the same commercial live vaccine (live attenuated vaccine against Canine Distemper, Adeno, Parvo and Parainfluenza virus) mixed with purified killed rabies virus component adjuvanted with either of two different Iscom-Matrix preparations i.e. MM703 and MB703 respectively (prepared as described in Example 1). At week 4, the Ferrets were boosted with the killed Rabies virus component alone (Group 1) or the Rabies component mixed with either of the two Matrix adjuvant preparations. The outline of the immunization is presented in Table 2.

Both the vaccines (freeze-dried live vaccine antigens and freeze-dried killed Rabies virus antigen) were reconstituted in either sterile PBS or sterile PBS supplemented with 75 μL/ml of either MM703 or MB703. Vaccines were administered subcutaneously according the manufacturer of the live vaccine. One ml vaccine was administered per dose.

TABLE 2

| Group | 1st vaccination (week 0) | 2nd vaccination (week 4) |
|---|---|---|
| 1 | Live vaccine + Killled Rabies | Killed Rabies |
| 2 | Live vaccine + Killed Rabies + MM703 | Killed Rabies + MM703 |
| 3 | Live vaccine + Killed Rabies + MB703 | Killed Rabies + MB703 |

The Ferrets were bled at week 0, 2, 4, 5, 6 and 8, and the sera were tested for antibodies against the vaccine components. The tests used were standard indirect ELISA used for routine sero-diagnostics and specially developed blocking ELISA's to confirm the specificity of the results Results The results are shown in Table 3 (indirect ELISA) and Table 4 (blocking ELISA).

Analyses in the conventional ELISA revealed that the serum antibody responses, were higher against both live antigens and against the killed rabies virus vaccine antigen in the animals immunized with the vaccine supplemented with the MM703 and MB703 formulations than in the control group, i.e. the animals in the group that was immunized with the non-adjuvanted vaccine.

Analyses by the blocking ELISA test showed that the CDV live antigen induced similar levels of serum antibody responses in all groups. The immune response to the other live vaccine antigens was enhanced both by MM703 and MB703 formulations. These adjuvant formulations enhanced considerably the serum antibody levels to the killed rabies virus vaccine antigen.

For none of the viruses tested did ferrets in the groups given a mixture of live virus and any of the two Matrix preparations respond with titres lower than the ferrets in group 1. Ferrets in group 1 were vaccinated with the live attenuated virus without Matrix adjuvant. Contrary, a surprisingly high number of ferrets that received the live vaccine mixed with either of the two Matrix adjuvants, responded with higher titres than those receiving non-adjuvanted live vaccine.

TABLE 3

Indirect ELISA analysis of serum samples from Ferrets vaccinated with a combination live viral vaccine and killed Rabies vaccine, with or without additional Iscom-Matrix Adjuvant.

| Groups | CAV wk 0 | CAV wk 2 | CAV wk 4 | CAV wk 5 | CAV wk 6 | CAV wk 8 | CDV wk 0 | CDV wk 2 | CDV wk 4 | CDV wk 5 | CDV wk 6 | CDV wk 8 |
|---|---|---|---|---|---|---|---|---|---|---|---|---|
| Control Group | | | | | | | | | | | | |
| Ferret #1 | 40 | 450 | 40 | 150 | 40 | 40 | 40 | 150 | 50 | 50 | 150 | 40 |
| Ferret #2 | 40 | 100 | 50 | 150 | 40 | 40 | 40 | 150 | 50 | 40 | 150 | 40 |
| Ferret #3 | 40 | 450 | 150 | 150 | 50 | 50 | 40 | 150 | 40 | 40 | 50 | 150 |

TABLE 3-continued Indirect ELISA analysis of serum samples from Ferrets vaccinated with a combination live viral vaccine and killed Rabies vaccine, with or without additional Iscom-Matrix Adjuvant.

| | | | | | | | | | | | | |
|---|---|---|---|---|---|---|---|---|---|---|---|---|
| Ferret #4 | 40 | 150 | 100 | 150 | 50 | 50 | 40 | 150 | 50 | 40 | 50 | 40 |
| Ferret #5 | 40 | 150 | 40 | 450 | 40 | 40 | 40 | 450 | 50 | 50 | 50 | 40 |
| Ferret #6 | 40 | 150 | 50 | 50 | 50 | 40 | 40 | 450 | 150 | 40 | 50 | 100 |
| MB703 | | | | | | | | | | | | |
| Ferret #7 | 40 | 450 | 450 | 2700 | 1350 | 1350 | 40 | 150 | 450 | 450 | 450 | 450 |
| Ferret #8 | 40 | 450 | 150 | 1350 | 450 | 450 | 40 | 150 | 50 | 50 | 50 | 40 |
| Ferret #9 | 40 | 450 | 1350 | 4050 | 2700 | 1350 | 40 | 450 | 450 | 450 | 450 | 150 |
| Ferret #10 | 40 | 50 | 40 | 1350 | 50 | 50 | 40 | 150 | 50 | 40 | 50 | 50 |
| Ferret #11 | 40 | 150 | 40 | 40 | 50 | 40 | 50 | 150 | 50 | 40 | 50 | 50 |
| Ferret #12 | 40 | 450 | 1350 | 4050 | 4050 | 2700 | 40 | 450 | 450 | 450 | 450 | 450 |
| MM703 | | | | | | | | | | | | |
| Ferret #13 | 40 | 50 | 450 | 1350 | 1350 | 150 | 40 | 150 | 150 | 50 | 150 | 50 |
| Ferret #14 | 40 | 150 | 1350 | 2700 | 12150 | 2700 | 40 | 150 | 150 | 450 | 450 | 450 |
| Ferret #15 | 40 | 450 | 50 | 40 | 40 | 40 | 40 | 50 | 50 | 40 | 40 | 40 |
| Ferret #16 | 450 | — | — | — | — | — | 40 | — | — | — | — | — |
| Ferret #17 | 40 | 50 | 1350 | 4050 | 2700 | 1350 | 40 | 450 | 450 | 450 | 150 | 150 |
| Ferret #18 | 40 | 150 | 40 | 40 | 50 | 50 | 40 | 1350 | 40 | 40 | 40 | 40 |

| Groups | CPV wk 0 | CPV wk 2 | CPV wk 4 | CPV wk 5 | CPV wk 6 | CPV wk 8 | CPI 5 wk 0 | CPI 5 wk 2 | CPI 5 wk 4 | CPI 5 wk 5 | CPI 5 wk 6 | CPI 5 wk 8 |
|---|---|---|---|---|---|---|---|---|---|---|---|---|
| Control Group | | | | | | | | | | | | |
| Ferret #1 | 40 | 40 | 450 | 450 | 40 | 50 | 40 | 150 | 40 | 50 | 40 | 40 |
| Ferret #2 | 40 | 40 | 450 | 450 | 40 | 150 | 40 | 150 | 40 | 50 | 40 | 40 |
| Ferret #3 | 40 | 150 | 300 | 450 | 50 | 40 | 40 | 150 | 40 | 50 | 40 | 40 |
| Ferret #4 | 450 | 150 | 450 | 1350 | 300 | 300 | 40 | 150 | 40 | 40 | 40 | 150 |
| Ferret #5 | 40 | 40 | 40 | 450 | 40 | 50 | 40 | 450 | 40 | 100 | 40 | 40 |
| Ferret #6 | 40 | 100 | 40 | 450 | 40 | 40 | 40 | 450 | 40 | 50 | 40 | 40 |
| MB703 | | | | | | | | | | | | |
| Ferret #7 | 40 | 1350 | 1350 | 4050 | 1350 | 4050 | 40 | 150 | 40 | 450 | 40 | 50 |
| Ferret #8 | 150 | 1350 | 1350 | 4050 | 1350 | 1350 | 40 | 150 | 40 | 40 | 40 | 40 |
| Ferret #9 | 100 | 4050 | 4050 | 12150 | 4050 | 4050 | 40 | 40 | 40 | 1350 | 150 | 50 |
| Ferret #10 | 150 | 450 | 1350 | 4050 | 450 | 1350 | 40 | 150 | 40 | 40 | 40 | 40 |
| Ferret #11 | 100 | 450 | 150 | 300 | 150 | 900 | 50 | 150 | 50 | 40 | 50 | 40 |
| Ferret #12 | 40 | 100 | 450 | 1350 | 450 | 1350 | 40 | 150 | 40 | 2700 | 1350 | 1350 |
| MM703 | | | | | | | | | | | | |
| Ferret #13 | 150 | 1350 | 4050 | 12150 | 12150 | 12150 | 40 | 100 | 40 | 40 | 40 | 40 |
| Ferret #14 | 150 | 1350 | 12150 | 12150 | 4050 | 12150 | 150 | 150 | 50 | 1350 | 1350 | 450 |
| Ferret #15 | 40 | 100 | 1350 | 4050 | 900 | 4050 | 40 | 100 | 50 | 40 | 40 | 40 |
| Ferret #16 | 40 | — | — | — | — | — | 40 | — | — | — | — | — |
| Ferret #17 | 100 | 100 | 450 | 4050 | 450 | 4050 | 40 | 50 | 50 | 1350 | 150 | 450 |
| Ferret #18 | 40 | 450 | 1350 | 4050 | 450 | 1350 | 40 | 450 | 40 | 450 | 40 | 40 |

| Groups | Rab wk 0 | Rab wk 2 | Rab wk 4 | Rab wk 5 | Rab wk 6 | Rab wk 8 |
|---|---|---|---|---|---|---|
| Control Group | | | | | | |
| Ferret #1 | 40 | 150 | 450 | 150 | 150 | 50 |
| Ferret #2 | 40 | 150 | 450 | 40 | 50 | 40 |
| Ferret #3 | 40 | 50 | 900 | 40 | 40 | 40 |
| Ferret #4 | 40 | 50 | 900 | 40 | 40 | 40 |
| Ferret #5 | 40 | 450 | 450 | 50 | 40 | 40 |
| Ferret #6 | 40 | 150 | 450 | 50 | 50 | 40 |
| MB703 | | | | | | |
| Ferret #7 | 40 | 1350 | 900 | 4050 | 4050 | 12150 |
| Ferret #8 | 40 | 900 | 450 | 900 | 12150 | 4050 |
| Ferret #9 | 40 | 1350 | 4050 | 4050 | 4050 | 1350 |
| Ferret #10 | 40 | 900 | 4050 | 4050 | 4050 | 1350 |
| Ferret #11 | 40 | 900 | 450 | 450 | 4050 | 4050 |
| Ferret #12 | 40 | 900 | 4050 | 12150 | 12150 | 12150 |
| MM703 | | | | | | |
| Ferret #13 | 40 | 1350 | 450 | 4050 | 12150 | 4050 |
| Ferret #14 | 40 | 1350 | 1350 | 12150 | 12150 | 4050 |
| Ferret #15 | 40 | 1350 | 150 | 900 | 4050 | 1350 |
| Ferret #16 | 40 | — | — | — | — | — |

TABLE 3-continued

Indirect ELISA analysis of serum samples from Ferrets vaccinated with a combination live viral vaccine and killed Rabies vaccine, with or without additional Iscom-Matrix Adjuvant.

| Ferret #17 | 40 | 1350 | 1350 | 12150 | 12150 | 4050 |
| Ferret #18 | 40 | 900 | 900 | 12150 | 12150 | 12150 |

1. All results are in Arbitrary Units (AU)
2. CAV = canine adenovirus, CDV = Canine distemper virus, CPV = canine parvovirus, CPI5 = canine parainfluenzavirus 5, Rab = rabies
3. — = no data

TABLE 4

Blocking ELISA analysis of serum samples from Ferrets vaccinated with a combination live viral vaccine and killed Rabies vaccine, with or without additional Iscom-Matrix Adjuvant.

| Groups | Rab wk 0 | Rab wk 2 | Rab wk 4 | Rab wk 5 | Rab wk 6 | Rab wk 8 | CAV wk 0 | CAV wk 2 | CAV wk 4 | CAV wk 5 | CAV wk 6 | CAV wk 8 |
|---|---|---|---|---|---|---|---|---|---|---|---|---|
| Control Group | | | | | | | | | | | | |
| Ferret #1 | <3 | 27 | <3 | <3 | <3 | 3 | <3 | <3 | <3 | <3 | <3 | <3 |
| Ferret #2 | <3 | 9 | <3 | <3 | <3 | <3 | <3 | <3 | <3 | <3 | <3 | <3 |
| Ferret #3 | <3 | 3 | <3 | <3 | <3 | <3 | <3 | <3 | <3 | <3 | <3 | <3 |
| Ferret #4 | <3 | 3 | 3 | <3 | <3 | <3 | <3 | <3 | <3 | <3 | <3 | <3 |
| Ferret #5 | <3 | 9 | 3 | <3 | <3 | <3 | <3 | <3 | <3 | <3 | <3 | <3 |
| Ferret #6 | <3 | 3 | 3 | <3 | <3 | <3 | <3 | <3 | <3 | <3 | <3 | <3 |
| MB703 | | | | | | | | | | | | |
| Ferret #7 | <3 | <3 | 9 |  | >81 | 9 | <3 | <3 | <3 | <3 | <3 | <3 |
| Ferret #8 | <3 | <3 | 3 | 9 | >81 | 9 | <3 | <3 | 9 | 9 | 9 | 3 |
| Ferret #9 | <3 | <3 | 9 | 54 | >81 | 27 | <3 | <3 | 27 | 81 | 27 | 9 |
| Ferret #10 | <3 | <3 | 3 | 9 | 27 | 27 | <3 | <3 | <3 | <3 | <3 | <3 |
| Ferret #11 | <3 | <3 | <3 | 9 | 9 | 27 | <3 | <3 | <3 | <3 | <3 | <3 |
| Ferret #12 | <3 | <3 | <3 | 81 | 81 | >=81 | <3 | <3 | <3 | <3 | <3 | <3 |
| MM703 | | | | | | | | | | | | |
| Ferret #13 | <3 | <3 | <3 | 3 | 9 | 27 | <3 | <3 | <3 | <3 | <3 | <3 |
| Ferret #14 | <3 | 3 | 3 | 81 | >81 | 27 | <3 | <3 | 9 | 27 | 27 | 3 |
| Ferret #15 | <3 | 9 | <3 | 3 | 9 | 27 | <3 | <3 | <3 | <3 | <3 | <3 |
| Ferret #16 | 3 | — | — | — | — | — | <3 | — | — | — | — | — |
| Ferret #17 | 3 | <3 | 3 | 18 | >81 | >=81 | <3 | <3 | <3 | <3 | <3 | <3 |
| Ferret #18 | 9 | <3 | <3 | 18 | >81 | >=81 | <3 | <3 | <3 | <3 | <3 |  |

| Groups | CDV wk 0 | CDV wk 2 | CDV wk 4 | CDV wk 5 | CDV wk 6 | CDV wk 8 | CPV wk 0 | CPV wk 2 | CPV wk 4 | CPV wk 5 | CPV wk 6 | CPV wk 8 |
|---|---|---|---|---|---|---|---|---|---|---|---|---|
| Control Group | | | | | | | | | | | | |
| Ferret #1 | <3 | <3 | 3 | <3 | <3 | 3 | <3 | <3 | <3 | <3 | <3 | <3 |
| Ferret #2 | <3 | <3 | <3 | <3 | <3 | 3 | <3 | <3 | <3 | <3 | 3 | <3 |
| Ferret #3 | <3 | <3 | <3 | <3 | 3 | 3 | <3 | 9 | <3 | <3 | <3 | <3 |
| Ferret #4 | <3 | <3 | 6 | <3 | 3 | 9 | <3 | <3 | 3 | <3 | <3 | <3 |
| Ferret #5 | <3 | 3 | 3 | <3 | <3 | 9 | <3 | <3 | <3 | <3 | <3 | <3 |
| Ferret #6 | <3 | <3 | <3, | 3 | <3 | 3 | <3 | <3 | <3 | <3 | <3 | <3 |
| MB703 | | | | | | | | | | | | |
| Ferret #7 | <3 | 3 | 6 | <3 | 3 | <3 | <3 | <3 | 9 | 3 | 27 | 27 |
| Ferret #8 | <3 | <3 | 3 | <3 | 3 | <3 | <3 | <3 | 3 | 9 | 3 | 9 |
| Ferret #9 | <3 | 3 | 6 | 6 | 6 | <3 | <3 | 9 | 54 | 3 | >81 | >81 |
| Ferret #10 | <3 | <3 | <3 | <3 | <3 | <3 | <3 | <3 | <3 | 3 | 3 | 54 |
| Ferret #11 | <3 | <3 | <3 | <3 | 3 | <3 | <3 | <3 | <3 | <3 | <3 | 3 |
| Ferret #12 | <3 | 9 | 3 | <3 | 9 | 3 | <3 | <3 | <3 | <3 | <3 | 9 |
| MM703 | | | | | | | | | | | | |
| Ferret #13 | <3 | <3 | <3 | <3 | <3 | <3 | 3 | 3 | <3 | 27 | >81 | >81 |
| Ferret #14 | <3 | <3 | <3 | 3 | 9 | 9 | <3 | 3 | 9 | <3 | 9 | >81 |
| Ferret #15 | <3 | <3 | <3 | 3 | <3 | 9 | <3 | 27 | <3 | <3 | 3 | 27 |
| Ferret #16 | <3 | 0 | 0 | 0 | 0 | 0 | 3 | 0 | 0 | 0 | 0 | 0 |
| Ferret #17 | <3 | 3 | 9 | 3 | <3 | <3 | <3 | <3 | <3 | <3 | <3 | 9 |
| Ferret #18 | <3 | 9 | <3 | 6 | <3 | 27 | <3 | <3 | <3 | <3 | <3 | 3 |

1. All results are in Titers
2. CAV = canine adenovirus, Rab = rabies virus, CDV = canine distemper virus, CPV = canine parvovirus
3. — = not tested Use of an iscom particle as adjuvant for preparing of an antigenic composition, which includes at least one live micro-organism, is disclosed. The antigenic composition can be a vaccine including at least one live virus. The antigenic composition further can include at least one killed or inactivated micro-organism. The antigenic composition further can include one or more antigenic molecules. The iscom particle can be an iscom that includes at least one glycoside, at least one lipid and at least one hydrophobic protein or peptide-containing antigen. The iscom particle also can be an iscom-matrix that includes at least one glycoside and at least one lipid. The iscom particle can include at least one glycoside fragment from Quil A. The iscom particle also can include subfragment A and/or subfragment C of Quil A.

Also disclosed is a composition that includes at least one iscom particle and one or more living micro-organisms. In the composition, the living micro-organism can be a virus. The composition can include one or more killed or inactivated micro-organisms. The composition further can include one or more antigenic molecules. In the composition, the iscom particle can include at least one glycoside fragment from Quil A. In the composition, the iscom particle also can include subfragment A and/or subfragment C of Quil A. The composition further can include a pharmaceutically acceptable carrier, diluent, excipient or additive.

Also disclosed is a kit of parts including at least one compartment containing at least one living organism and at least one compartment containing at least one iscom particle. The kit of parts further can include at least one inactivated micro-organism, which may be present in a further compartment or in the same compartment as the at least one compartment containing the at least one iscom particle.

The invention claimed is:

1. A method of preparing an antigenic composition, comprising mixing an iscom particle and at least one live attenuated micro-organism, wherein the iscom particle is used as an adjuvant, and wherein the live attenuate micro-organism is selected from the group consisting of: Canine distemper virus, Canine parvovirus, Canine adenovirus, *Bordetella bronchiseptica*, Canine Parainfluenza 3 virus, Feline parvovirus, Feline calici virus, Feline herpesvirus, *Chlamydia psittaci*, varicella virus, *mycobacterium bovis, Salmonella typhi*, a *Shigella* spp, and *vibrio cholera*, or mixtures thereof.

2. The method according to claim 1, wherein the antigenic composition is a vaccine comprising at least one live virus.

3. The method according to claim 1, wherein the antigenic composition further comprises at least one killed or inactivated micro-organism.

4. The method according to claim 1, wherein the antigenic composition further comprises at least one antigenic molecule.

5. The method according to claim 1, wherein the iscom particle is an iscom comprising at least one glycoside, at least one lipid and at least one hydrophobic protein or peptide-containing antigen.

6. The method according to claim 1, wherein the iscom particle is an iscom-matrix, comprising at least one glycoside and at least one lipid.

7. The method according to claim 6, wherein the iscom particle comprises at least one of Fraction A and Fraction C of *Quillaja Saponaria* Molina.

8. The method according to claim 1, wherein the iscom particle comprises at least one glycoside fragment from *Quillaja Saponaria* Molina.

9. The method according to claim 1, wherein the method includes providing a kit of parts comprising at least one compartment containing the at least one live micro-organism and at least one compartment containing the iscom particle.

10. The method according to any of claims 1-6, wherein a plurality of the iscom particles comprise a first iscom particle and a second iscom particle, the first iscom particle comprising a first fraction of *Quillaja Saponaria* Molina and not a second fraction of *Quillaja Saponaria* Molina, and the second iscom particle comprising the second fraction of *Quillaja Saponaria* Molina and not the first fraction of *Quillaja Saponaria* Molina.

11. A vaccine composition comprising at least one iscom particle, wherein the iscom particle is used as an adjuvant, and at least one live attenuated micro-organism wherein the live attenuated micro-organism is selected from the group consisting of: Canine distemper virus, Canine parvovirus, Canine adenovirus, *Bordetella bronchiseptica*, Canine Parainfluenza 3 virus, Feline parvovirus, Feline calici virus, Feline herpesvirus, *Chlamydia psittaci*, varicella virus, *mycobacterium bovis, Salmonella typhi*, a *Shigella* spp, and *vibrio cholera*, or mixtures thereof.

12. Composition according to claim 11, wherein the live micro-organism is a virus.

13. Composition according to claim 11, further comprising at least one killed or inactivated micro-organism.

14. Composition according to claim 11, further comprising at least one antigenic molecule.

15. Composition according to claim 11, wherein the iscom particle comprises at least one glycoside fragment from *Quillaja Saponaria* Molina.

16. Composition according to any of claims 11-15, wherein the iscom particle comprises at least one of Fraction A and Fraction C of *Quillaja Saponaria* Molina.

17. Composition according to claim 11, further comprising a pharmaceutically acceptable carrier, diluent, excipient or additive.

18. The composition according to claim 11, wherein the iscom particle is an iscom comprising at least one glycoside, at least one lipid and at least one hydrophobic protein or peptide-containing antigen.

19. The composition according to claim 11, wherein the iscom particle is an iscom-matrix, comprising at least one glycoside and at least one lipid.

20. The composition according to any of claim 11-14 or 18-19, wherein a plurality of the iscom particles comprise a first iscom particle and a second iscom particle, the first iscom particle comprising a first fraction of *Quillaja Saponaria* Molina and not a second fraction of *Quillaja Saponaria* Molina, and the second iscom particle comprising the second fraction of *Quillaja Saponaria* Molina and not the first fraction of *Quillaja Saponaria* Molina.

21. The composition according to claim 11, wherein the composition may be used for humans.

22. The composition according to claim 11, wherein the composition does not reduce proliferation of the live attenuated micro-organism in a host.

23. The composition according to claim 11, wherein the composition provides for enhanced immunogenicity of the live micro-organism in a host.

* * * * *